US009682071B2

(12) United States Patent
Nicolls et al.

(10) Patent No.: US 9,682,071 B2
(45) Date of Patent: Jun. 20, 2017

(54) METHODS OF IMPROVING MICROVASCULAR INTEGRITY

(71) Applicants: INTERMUNE, INC., Brisbane, CA (US); THE BOARD OF TRUSTEES OF THE LELAND STANFORD JUNIOR UNIVERSITY, Palo Alto, CA (US); THE UNITED STATES OF AMERICA AS REPRESENTED BY THE DEPARTMENT OF VETERANS AFFAIRS, Washington, DC (US)

(72) Inventors: Mark R. Nicolls, Palo Alto, CA (US); Karl Kossen, Brisbane, CA (US); Alan Cohen, Menlo Park, CA (US)

(73) Assignees: INTERMUNE, INC., Brisbane, CA (US); THE BOARD OF TRUSTEES OF THE LELAND STANFORD, Palo Alto, CA (US)

(*) Notice: Subject to any disclaimer, the term of this patent is extended or adjusted under 35 U.S.C. 154(b) by 0 days.

(21) Appl. No.: 14/772,241

(22) PCT Filed: Mar. 13, 2014

(86) PCT No.: PCT/US2014/025895
§ 371 (c)(1),
(2) Date: Sep. 2, 2015

(87) PCT Pub. No.: WO2014/151517
PCT Pub. Date: Sep. 25, 2014

(65) Prior Publication Data
US 2016/0022654 A1 Jan. 28, 2016

Related U.S. Application Data

(60) Provisional application No. 61/793,035, filed on Mar. 15, 2013.

(51) Int. Cl.
*A61K 31/4418* (2006.01)
*A61K 31/437* (2006.01)
*A61K 31/4412* (2006.01)
*A61K 31/4427* (2006.01)
*A61K 45/06* (2006.01)

(52) U.S. Cl.
CPC ........ *A61K 31/4418* (2013.01); *A61K 31/437* (2013.01); *A61K 31/4412* (2013.01); *A61K 31/4427* (2013.01); *A61K 45/06* (2013.01)

(58) Field of Classification Search
None
See application file for complete search history.

(56) References Cited

U.S. PATENT DOCUMENTS

| 4,120,649 | A | 10/1978 | Schechter |
| 4,665,077 | A | 5/1987 | Stringfellow et al. |
| 5,114,721 | A | 5/1992 | Cohen et al. |
| 7,189,518 | B2* | 3/2007 | Schonbeck ........ A61K 38/1709 435/7.1 |
| 7,635,707 | B1 | 12/2009 | Bradford et al. |
| 7,728,013 | B2 | 6/2010 | Blatt et al. |
| 2003/0152566 | A1 | 8/2003 | Schonbeck et al. |
| 2006/0069020 | A1 | 3/2006 | Blair et al. |
| 2007/0117841 | A1 | 5/2007 | Ozes et al. |
| 2010/0190731 | A1 | 7/2010 | Olgin et al. |
| 2012/0258924 | A1 | 10/2012 | Blatt et al. |
| 2013/0045997 | A1 | 2/2013 | Bradford et al. |
| 2014/0249347 | A1 | 9/2014 | Wu |

FOREIGN PATENT DOCUMENTS

| EP | 340109 A2 | 11/1989 |
| WO | WO-90/8187 A1 | 7/1990 |
| WO | WO-90/11294 A1 | 10/1990 |
| WO | WO-91/01133 A1 | 2/1991 |
| WO | WO-2007038315 A2 | 4/2007 |
| WO | WO-2007/064738 A1 | 6/2007 |
| WO | WO-2008/077068 A1 | 6/2008 |
| WO | WO-2009/035598 A1 | 3/2009 |
| WO | WO-2010/054294 A1 | 5/2010 |
| WO | WO-2011/069089 A1 | 6/2011 |
| WO | WO-2011/069094 A1 | 6/2011 |
| WO | WO-2012/106382 A1 | 8/2012 |
| WO | WO-2014/036487 A1 | 3/2014 |

OTHER PUBLICATIONS

Babu et al., Microvascular destruction identifies murine allografts that cannot be rescued from airway fibrosis, *J Clin Invest.*, 117(12):3774-85 (2007).
Dauber et al., Functional coronary microvascular injury evident as increased permeability due to brief ischemia and reperfusion, *Circ. Res.*, 66:986-98 (1990).
Engelbrecht et al., Contrast-enhanced 3D-TOF MRA of peripheral vessels: intravascular versus extracellular MR contrast media, *J. Magn. Reson. Imaging.*, 8:616-21 (1998).
International Search Report and Written Opinion of the International Search Authority, United States Patent Office, PCT/US2014/25895, dated Jul. 17, 2014.
International Preliminary Report on Patentability, United States Patent Office, PCT/US2014/25895, dated Sep. 15, 2015.
Janeway, Autoimmune disease: immunotherapy by peptides? *Nature*, 341:482-483 (1989).
Jiang et al., Adenovirus-mediated HIF-1α gene transfer promotes repair of mouse airway allograft microvasculature and attenuates chronic rejection, *J. Clin. Invest.*, 121(6):2336-49 (2011).
Lim et al., Occlusive and reperfused myocardial infarction: detection by using MR imaging with gadolinium polylysine enhancement, *Radiology*, 189:765-8 (1993).

(Continued)

*Primary Examiner* — Heidi Reese
(74) *Attorney, Agent, or Firm* — Marshall, Gerstein & Borun LLP

(57) ABSTRACT

The disclosure relates to methods of preserving or improving microvascular integrity in a patient in need thereof comprising administering pirfenidone therapy to the patient.

3 Claims, 3 Drawing Sheets

(56) References Cited

OTHER PUBLICATIONS

McDonagh et al., Prevention of transcoronary macromolecular leakage after ischemia-reperfusion by the calcium entry blocker nisoldipine. Direct observations in isolated rat hearts, *Circ. Res.*, 58:127-36 (1986).

Offner et al., T cell receptor peptide therapy triggers autoregulation of experimental encephalomyelitis. *Science*, 251:430-432 (1991).

Schwitter et al., Influence of severity of myocardial injury on distribution of macromolecules: extravascular versus intravascular gadolinium-based magnetic resonance contrast agents, *J. Am. Coll. Cardiol.*, 30:1086-94 (1997).

Semenza, Regulation of oxygen homeostasis by hypoxia-inducible factor 1, *Physiology(Bethesda)*, 24:97-106 (2009).

Zeisberg et al. 'Mechanisms of Tubulointerestital Eibrosis' *J. Am. Soc. Nephrol.*, 21:1819-34.

Bizargity, et al. "Inhibitory Effects of Pirfenidone on Dendritic Cells and Lung Allograft Rejection," Transplantation 94(2):1-9 (2012).

Contreras, et al. "Every allograft needs a silver lining," The Journal of Clinical Investigation 117(12):3645-3648 (2007).

Iyer, et al. "Lung Fibrosis is Ameliorated by Pirfenidone Fed in Diet After the Second Dose in a Three-Dose Bleomycin-Hamster Model," Experimental Lung Research 24:119-132 (1998).

McKane, et al. "Pirfenidone Inhibits Obliterative Airway Disease in a Murine Heterotopic Tracheal Transplant Model," Transplantation 77(5):664-669 (2004).

Oku, et al. "Antifibrotic action of pirfenidone and prednisolone: Different effects on pulmonary cytokines and growth factors in bleomycin-induced murine pulmonary fibrosis," European Journal of Pharmacology 590:400-408 (2008).

Schaefer, et al. "Antifibrotic activities of pirfenidone in animal models," Eur Respir Rev 20(120):85-97 (2011).

Shimizu, et al. "Pirfenidone improves renal function and fibrosis in the post-obstructed kidney," Kidney International, 54:99-109 (1998).

Tada, et al. "Pirfenidone Inhibits Dimethylnitrosamine-Induced Hepatic Fibrosis in Rats," Clinical and Experimental Pharmacology and Physiology 28:522-527 (2001).

Woodruff, et al. "Inhibiting the C5-C5a receptor axis," Molecular Immunology 48:1631-1642 (2011).

Zhou, et al. "Pirfenidone Inhibits Obliterative Airway Disease in Mouse Tracheal Allografts," The Journal of Heart and Lung Transplantation, 24(10):1577-1585 (2005).

Dosanjh "Pirfenidone: A Novel Potential Therapeutic Agent in the Management of Chronic Allograft Rejection," Transplantation Proceedings, 39:2153-2156 (2007).

Dosanjh "Pirfenidone: Anti-fibrotic agent with a potential therapeutic role in the management of transplantation patients," European Journal of Pharmacology 536:219-222 (2006).

Kai-Ming, et al. "Microvascular Targets for Anti-Fibrotic Therapeutics," Yale Journal of Biology and Medicine 86:537-554 (2013).

Visner, et al. "Pirfenidone Inhibits T-Cell Activation, Proliferation, Cytokine and Chemokine Production, and Host Alloresponses," Transplantation 88(3):330-338 (2009).

* cited by examiner

METHODS OF IMPROVING MICROVASCULAR INTEGRITY

CROSS-REFERENCE TO RELATED APPLICATIONS

This application is a U.S. National Phase of International Application No. PCT/US2014/025895 filed Mar. 13, 2014, which claims priority benefit of U.S. Provisional Patent Application No. 61/793,035 filed Mar. 15, 2013, each of which is incorporated herein by reference in their entireties.

FIELD OF THE INVENTION

The disclosure relates to methods of preserving or improving microvascular integrity in a patient in need thereof comprising administering pirfenidone therapy to the patient.

BACKGROUND

Pirfenidone is small molecule with a molecular weight of 185.23 daltons whose chemical name is 5-methyl-1-phenyl-2-(1H)-pyridone. Pirfenidone has anti-fibrotic properties and has been investigated for therapeutic benefits to patients suffering from various fibrotic conditions. It is approved in Japan for treatment of idiopathic pulmonary fibrosis (IPF) under the trade name Pirespa®, and in several European countries under the trade name Esbriet®.

Microvascular integrity and injury to the microvasculature is characterized by leakage of plasma macromolecules and can be observed even after mild ischemic insult [Dauber et al., *Circ Res* 66: 986-98 (1990); McDonagh et al., *Circ Res* 58: 127-36 (1986)]. Ischemia is the principal stimulus that induces neovascularization [Semenza, *Physiology* (Bethesda) 24: 97-106 (2009)]. Recent work has shown the importance of the microvasculature in the long-term survival of solid organ transplants [Jiang et al., *J Clin Invest* 121(6): 2336-49 (2011), incorporated by reference herein in its entirety].

SUMMARY OF THE INVENTION

The disclosure generally relates to methods of preserving or improving microvascular integrity and treating a microvascular disorder comprising administering pirfenidone to a patient, and to corresponding methods of preparing or packaging pirfenidone medicaments, containers, packages and kits.

The present disclosure is based on the discovery that administration of pirfenidone preserves microvasculature integrity. In a trachea allograft mouse model of acute transplant rejection, vascular perfusion and tissue oxygenation (as measured by $pO_2$) begin dramatically decreasing by day 6 post-transplantation; by day 10, perfusion is completely lost. Surprisingly, treatment with pirfenidone prevents microvasculature impairment, maintaining tissue oxygenation levels at the same levels through at least day 12. This novel observation of the effects of pirfenidone permits a variety of novel uses for pirfenidone outside of its prior role as an anti-fibrotic agent. According to any of the aspects disclosed herein, pirfenidone or a pirfenidone analog is administered to a patient with deteriorating microvascularization, in need of improved vascularization, or who would benefit from improved or preserved microvasculature integrity.

In one aspect of the disclosure, administration of pirfenidone or a pirfenidone analog to a patient with an acute organ or tissue injury, prior to diagnosis and/or onset and/or showing signs or symptoms of fibrosis, preserves or improves microvascular integrity. For example, the administration may occur prior to an acute insult or injury, or within 2, 3, 4, 5, 6, or 7 days of the acute insult or injury. The preservation or improvement in microvascular integrity results in a reduction in severity, symptoms or sequelae of the acute insult or injury.

Thus, the disclosure provides a method for preserving or improving microvascular integrity comprising administering pirfenidone, or an analog thereof, to a patient with an acute organ or tissue injury prior to diagnosis/onset/showing signs or symptoms of fibrosis, and wherein the pirfenidone or analog thereof is administered in an amount effective to preserve or improve microvascular integrity. In a related aspect, the disclosure provides a use of pirfenidone, or an analog thereof, in the manufacture of a medicament for preserving or improving microvascular integrity, wherein the medicament is for administering to a patient with an acute organ or tissue injury prior to diagnosis/onset/showing signs or symptoms of fibrosis, and wherein the medicament is administered in an amount effective to preserve or improve microvascular integrity.

In another aspect of the disclosure, administration of pirfenidone or a pirfenidone analog can treat new diseases or disorders not associated with fibrosis, e.g. microvascular disorders. Thus, a method is provided for treating a microvascular disorder comprising administering pirfenidone, or an analog thereof, to a patient with a microvascular disorder, and wherein the pirfenidone or analog thereof is administered in an amount effective to treat the microvascular disorder. In such an aspect, the microvascular disorder is not a fibrosis disorder. In a related aspect, the disclosure provides a use of pirfenidone, or an analog thereof, in the manufacture of a medicament for treating a microvascular disorder, wherein the medicament is for administering to a patient with a microvascular disorder (that is not a fibrosis disorder), and wherein the medicament is administered in an amount effective to treat the microvascular disorder.

In any of one of the methods or uses described herein, the pirfenidone analog is a compound of formula (I), (II), (III), (IV), or (V):

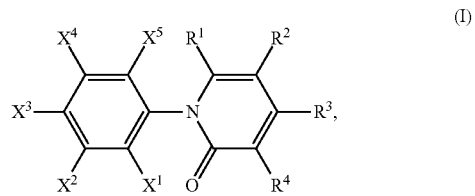

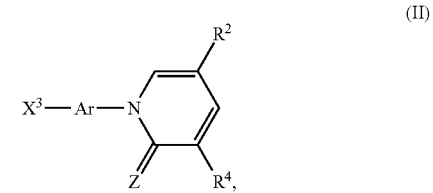

-continued

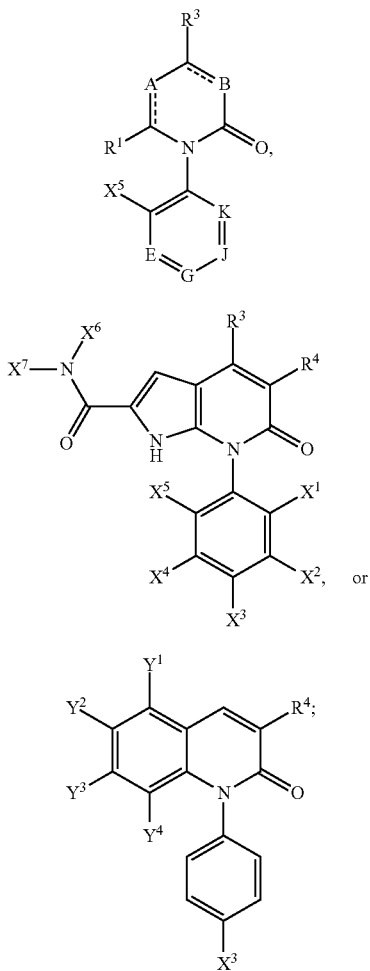

wherein $R^1, R^2, R^3, R^4, X^1, X^2, X^3, X^4, X^5, Y^1, Y^2, Y^3$, and $Y^4$ are independently selected from the group consisting of H, deuterium, $C_1$-$C_{10}$ alkyl, $C_1$-$C_{10}$ deuterated alkyl, substituted $C_1$-$C_{10}$ alkyl, $C_1$-$C_{10}$ alkenyl, substituted $C_1$-$C_{10}$ alkenyl, $C_1$-$C_{10}$ thioalkyl, $C_1$-$C_{10}$ alkoxy, substituted alkoxy, cycloalkyl, substituted cycloalkyl, heterocycloalkyl, substituted heterocycloalkyl, heteroalkyl, substituted heteroalkyl, aryl, substituted aryl, heteroaryl, substituted heteroaryl, halogen, hydroxyl, $C_1$-$C_{10}$ alkoxyalkyl, $C_1$-$C_{10}$ carboxy, $C_1$-$C_{10}$ alkoxycarbonyl, CO-uronide, CO-monosaccharide, CO-oligosaccharide, and CO-polysaccharide;

$X^6$ and $X^7$ are independently selected from the group consisting of hydrogen, aryl, substituted aryl, heteroaryl, substituted heteroaryl, cycloalkyl, substituted cycloalkyl, heterocycloalkyl, substituted heterocycloalkyl, alkylenylaryl, alkylenylheteroaryl, alkylenylheterocycloalkyl, alkylenylcycloalkyl, or $X^6$ and $X^7$ together form an optionally substituted 5 or 6 membered heterocyclic ring; and Ar is pyridinyl or phenyl; and Z is O or S.

In any of the aspects of the disclosure, a method is provided for treating a microvascular disorder comprising administering a deuterated pirfenidone (as described e.g., in WO09/035598 and having one to fourteen deuterium atoms replacing a hydrogen atom in pirfenidone), to a patient with a microvascular disorder, and wherein the deuterated pirfenidone is administered in an amount effective to treat the microvascular disorder.

In any of the methods or uses described herein, the patient may suffer from a disease selected from the group consisting of lung transplantation/chronic rejection, bronchiolitis obliterans, scleroderma, Primary focal segmental glomerulosclerosis (FSGS), membranoproliferative glomerulonephritis (MPGN), Pneumotosis intestinalis, Susac's syndrome, microvascular impairment during chronic catheterization, Hamartomatous disease, blood spinal cord barrier dysfunction following spinal cord injury, corneal perforation, paraneoplastic disease, rhabdomyolysis, pulmonary capillaritis, chronic hyperhomocysteinemia, frontal-subcortical syndrome, Wegener's granulomatosis, acute intestinal microvascular dysfunction, atherosclerotic disease, keratitis, episcleritis/scleritis, cystic fibrosis, polycystic kidney disease, sickle cell disease, dementia, diabetic ulcer, microangiopathy or small vessel disease, hypothyroidism, thrombotic thrombocytopenic purpura, ischemia-reperfusion injury and haemolytic uraemic syndrome. In one embodiment, the patient suffers from a dementia that is not Alzheimer's Disease. In another embodiment, the patient suffers from microangiopathy or small vessel disease that is not related to diabetes.

In further embodiments, the patient suffers from a disease selected from the group consisting of Pneumotosis intestinalis, Susac's syndrome, microvascular impairment during chronic catheterization, Hamartomatous disease, Blood spinal cord barrier dysfunction following spinal cord injury, corneal perforation, paraneoplastic disease, rhabdomyolysis, pulmonary capillaritis, chronic hyperhomocysteinemia, frontal-subcortical syndrome, Wegener's granulomatosis and acute intestinal microvascular dysfunction. Such disorders are not generally associated with fibrosis.

For example, according to any of the embodiments, the patient may suffer from an atherosclerotic disease, including but not limited to atherosclerosis of the renal vasculature, cardiac vasculature, brain vasculature and/or peripheral vasculature. As another example, according to any of the embodiments, the patient may suffer from thrombosis, an acute ischemic event, surgery, or an acute tissue injury. In some embodiments, patients specifically with acute myocardial infarction, lung transplantation, and/or wound healing are excluded.

In any of the aspects or embodiments, the amount effective to preserve or improve microvascular integrity or treat the microvascular disorder is about 2400 or 2403 mg/day. In any of the aspects of the disclosure, the daily dosage may be administered in divided doses three times a day, or two times a day, or alternatively is administered in a single dose once a day. In any of the aspects of the disclosure, the pirfenidone may be administered with food. For example, a daily oral dosage of 2400 mg or 2403 mg pirfenidone per day may be administered as follows: 800 mg or 801 mg taken three times a day, with food. Similarly, a daily oral dosage of 1600 mg or 1602 mg pirfenidone per day may be administered as 534 mg taken three times a day, with food. In any of the embodiments, the pirfenidone may be administered in oral unit dosage forms, e.g. capsules or tablets. In any of the embodiments, the amount of pirfenidone in the unit dosage form can be 200 mg or 267 mg.

Pirfenidone or a pirfenidone analog may be administered by a variety of routes, e.g. intravenous, intraarterial, intrapulmonary, subcutaneous, intramuscular, locally via catheter, applied to the skin, applied to mucosal membranes, or orally.

In any of the aspects or embodiments, the disclosure contemplates administering an additional therapeutic agent beneficial for the disorder. For example, the additional therapeutic can be selected from the group consisting of an immunosuppressive agent, an antioxidant or antioxidant gene regulator, and an anti-inflammatory agent.

The immunosuppressive agent, in various embodiments, may be selected from the group consisting of a steroid, cyclosporine, cyclosporine analogs, cyclophosphamide methylprednisone, prednisone, azathioprine, tacrolimus (FK-506), 15-deoxyspergualin, rapamycin, mycophenolic acid and sirolimus.

The antioxidant or antioxidant gene regulator, in various embodiments, may be selected from the group consisting of vitamin C, vitamin E, beta-carotene, new Ets-related factor-2 (NERF-2), N-acetyl cysteine (NAC), bardoxolone, lutein, zinc, selenium and copper.

The anti-inflammatory agent, in various embodiments, may be selected from the group consisting of azithromycin, a nonsteroidal anti-inflammatory drug (NSAID) a steroidal anti-inflammatory drug (SAID), a tumor necrosis factor (TNF) inhibitor, and an anti-inflammatory cytokine. The anti-inflammatory cytokine may be selected from the group consisting of IL-10 and IL-11.

In any of the aspects of the disclosure, the methods or uses further comprise administering to the patient a therapeutically effective amount of a hypoxia inducible factor-prolyl hydroxylase inhibitor (HIF-PHI).

In any aspect or embodiment of the disclosure, the additional therapeutic agent is selected from the group comprising one or more of steroids (including but not limited to prednisolone), cytotoxic agents (including but not limited to azathioprine and cyclophosphamide), bardoxolone, LPA antagonists, for example LPA1 (including but not limited to AM152); Torisel (temsirolimus); PI3K inhibitors (including but not limited to GSK2126458); pentraxin (including but not limited to Pentraxin-2 (PTX-2 or PRM-151)); MEK inhibitors (including but not limited to ARRY-162 and ARRY-300); p38 inhibitors; PAI-1 inhibitors (including but not limited to Tiplaxtinin); agents that reduce the activity of transforming growth factor-beta (TGF-β) (including but not limited to pan TGF-β neutralizing antibodies, such as GC-1008 (Genzyme/Medlmmune); anti-TGF-β2 mAbs, such as lerdelimumab (CAT-152; Trabio, Cambridge Antibody); anti-TGF-β1 antibodies, such as metelimumab (CAT-192, Cambridge Antibody); small molecule TGF-βR1 inhibitors, such as LY-2157299 (Eli Lilly); ACU-HTR-028 (Opko Health)) including antibodies that target one or more TGF-β isoforms, inhibitors of TGF-β receptor kinases TGFBR1 (ALK5) and TGFBR2, and modulators of post-receptor signaling pathways; modulators of chemokine receptor signaling; endothelin receptor antagonists including inhibitors that target both endothelin receptor A and B and those that selectively target endothelin receptor A (including but not limited to ambrisentan; avosentan; bosentan; clazosentan; darusentan; BQ-153; FR-139317, L-744453; macitentan; PD-145065; PD-156252; PD163610; PS-433540; S-0139; sitaxentan sodium; TBC-3711; zibotentan); agents that reduce the activity of connective tissue growth factor (CTGF) (including but not limited to FG-3019, FibroGen), and also including other CTGF-neutralizing antibodies, such as FG-3019; matrix metalloproteinase (MMP) inhibitors (including but not limited to MMPI-12, PUP-1 and tigapotide triflutate, and doxycycline, marimastat, and cipemastat); agents that reduce the activity of epidermal growth factor receptor (EGFR) including but not limed to erlotinib, gefitinib, BMS-690514, cetuximab, antibodies targeting EGF receptor, inhibitors of EGF receptor kinase, and modulators of post-receptor signaling pathways; agents that reduce the activity of platelet derived growth factor (PDGF) (including but not limited to Imatinib mesylate (Novartis)) and also including PDGF neutralizing antibodies, antibodies targeting PDGF receptor (PDGFR), inhibitors of PDGFR kinase activity, and post-receptor signaling pathways; inhibitors of multiple receptor kinases such as BIBF-1120 which inhibits receptor kinases for vascular endothelial growth factor, fibroblast growth factor, and platelet derived growth factor; agents that interfere with integrin function (including but not limited to STX-100 and IMGN-388) and also including integrin targeted antibodies; agents that interfere with the pro-fibrotic activities of IL-4 (including but not limited to AER-001, AMG-317, APG-201, and sIL-4Rα) and IL-13 (including but not limited to AER-001, AMG-317, anrukinzumab, CAT-354, cintredekin besudotox, MK-6105, QAX-576, SB-313, SL-102, and TNX-650) and also including neutralizing antibodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly pseudomonas endotoxin, signaling though the JAK-STAT kinase pathway; agents that interfere with epithelial mesenchymal transition including inhibitors of mTor (including but not limited to AP-23573 or rapamycin); agents that reduce oxidative stress including N-acetyl cysteine and tetrathiomolybdate; and interferon gamma. Also contemplated are agents that are inhibitors of phosphodiesterase 4 (PDE4) (including but not limited to Roflumilast); inhibitors of phosphodiesterase 5 (PDE5) (including but not limited to mirodenafil, PF-4480682, sildenafil citrate, SLx-2101, tadalafil, udenafil, UK-369003, vardenafil, and zaprinast); or modifiers of the arachidonic acid pathway including cyclooxygenase and 5-lipoxegenase inhibitors (including but not limited to Zileuton). Further contemplated are compounds that reduce tissue remodeling or fibrosis including prolyl hydrolase inhibitors (including but not limited to 1016548, CG-0089, FG-2216, FG-4497, FG-5615, FG-6513, fibrostatin A (Takeda), lufironil, P-1894B, and safironil) and peroxisome proliferator-activated receptor (PPAR)-gamma agonists (including but not limited to pioglitazone and rosiglitazone). Agents also include an agent selected from BG-12, chemokine activity modulators (including but not limited to CNTO 888, an antibody targeting CCL2), Lysl oxidase inhibitors (including but not limited to AB0024/GS-6624, an antibody targeting human lysyl oxidase-like 2), NOX4 inhibitors (including but not limited to GKT137831, a selective NOX $1/4$ inhibitor), angiotensin II receptor antagonists (including but not limited to lorsartan), and an LPA1/LPA3 antagonist (including but not limited to SAR-100842).

In any aspect disclosed herein, the methods or uses further comprise administering to the patient a therapeutically effective amount of a complement inhibitor. In some embodiments, the complement inhibitor is selected from the group consisting of Eculizumab/Soliris (Alexion), Pexelizumab (Alexion), Mubodina (Adienne), Ergidina (Adienne), ARC1905 (Archemix/Ophthotech), C5aIP/Pep-A (Tohoku University), TNX-558 (Tanox/Genentech), MBP-C5a (Resistentia/Karolinska Institute), C089 (Merck), 3D53/PMX53 (Promics/Cephalon), PMX205 (Promics/Cephalon), JPE-1375 (Jerini), JSM-7717 (Jerini), CGS 27913 (Novartis), CGS 32359 (Novartis), $A8^{\Delta 71-73}$ (Medical School Hannover), W-54011 (Mitsubishi Pharma), NDT 9520492 (Neurogen), NGD-2000-1 (Neurogen), NDT 9513727 (Neurogen), a non-peptide CD88 antagonist, CCX168 (ChemoCentryx), NOX-D14 (Noxxon Pharma), Neutrazumab (G2 Therapies/Novo Nodisk), ADC-1004 (Alligator Bioscience), comstatin, a C3, C5 or C5a inhibitor peptide, a C3, C5 or C5a antibody and fragments thereof.

In preferred embodiments, the additional therapeutic agent also preserves or improves microvascular integrity and/or function. A combination of any of the therapeutic agents provided herein is also contemplated.

In another aspect, the disclosure provides a package or kit comprising (a) pirfenidone or a pirfenidone analog, optionally in a container, and (b) a package insert, package label, instructions or other labeling directing or disclosing any of the methods or embodiments disclosed herein.

While in the present aspects and embodiments mammals may be treated, preferably the patient is a human.

DETAILED DESCRIPTION OF THE INVENTION

Figure 1A:
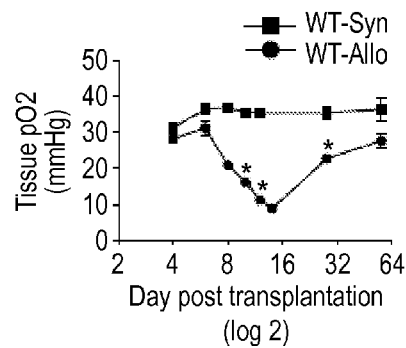
FIG. 1A shows tissue oxygenation levels ($pO_2$ in mmHg) in mice receiving syngeneic tracheal grafts (WT-Syn) and mice receiving allogeneic tracheal grafts (WT-Allo), plotted over time (days post transplantation).

Pirfenidone is an orally active, anti-fibrotic agent. Data reported herein show that pirfenidone preserves or improves the microvasculature (i.e., microvascular integrity) and is therefore useful in treatment, amelioration or prophylaxis of microvascular disorders.

The invention generally relates to uses and methods of administering pirfenidone or a pirfenidone analog to a patient with deteriorating microvascularization, in need of improved vascularization, or who would benefit from improved or preserved microvasculature integrity, and to methods of preparing or packaging pirfenidone or pirfenidone analog medicaments, containers, packages and kits. In any of the aspects of the disclosure, the pirfenidone or pirfenidone analog is for preserving or improving microvascular integrity and/or treating a microvascular disorder.

Definitions

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA), a "therapeutically effective amount" refers to the dosage approved by the FDA or its counterpart foreign agency for treatment of the identified disease or condition.

As used herein, a patient "in need of pirfenidone therapy" is a patient who would benefit from administration of pirfenidone or pirfenidone analog to improve/preserve microvascular integrity or treat a microvascular disorder. By "improve microvascular integrity" is meant that the microvascular permeability is decreased (or does not increase) in a patient receiving pirfenidone or a pirfenidone analog compared to a patient that is not receiving pirfenidone or a pirfenidone analog. By "preserving microvascular integrity" is meant that the decline in microvascular function caused by an acute injury or insult is reduced in a patient receiving pirfenidone or a pirfenidone analog compared to a patient that is not receiving pirfenidone or a pirfenidone analog. Measurement of microvascular integrity is known to those of skill in the art and can be determined by methods known in the art. By way of non-limiting example, microvascular integrity has been studied in vivo in organs such as the heart with magnetic resonance imaging (MRI) using macromolecular gadolinium chelates like GdDTPA-albumin or GdDTPA-polylysine [Lim et al., *Radiology* 189: 765-8 (1993); Saeed et al., *J Magn Reson Imaging* 8: 616-21 (1998); Schwitter et al., *J Am Coll Cardiol* 30: 1086-94 (1997)]. Macromolecules such as GdDTPA-albumin are retained in the vasculature in normal myocardium, but leak into the interstitium in reperfused infarction; this causes a relatively increased quantity of GdDTPA-albumin within the injured region [Saeed et al., *J Magn Reson Imaging* 8: 616-21 (1998)].

The patient can be a patient that suffers from a disease selected from the group consisting of lung transplantation/chronic rejection, bronchiolitis obliterans, scleroderma, Primary focal segmental glomerulosclerosis (FSGS), membranoproliferative glomerulonephritis (MPGN), Pneumotosis intestinalis, Susac's syndrome, microvascular impairment during chronic catheterization, Hamartomatous disease, blood spinal cord barrier dysfunction following spinal cord injury, corneal perforation, paraneoplastic disease, rhabdomyolysis, pulmonary capillaritis, chronic hyperhomocysteinemia, frontal-subcortical syndrome, Wegener's granulomatosis, acute intestinal microvascular dysfunction, atherosclerotic disease, keratitis, episcleritis/scleritis, cystic fibrosis, polycystic kidney disease, sickle cell disease, dementia, diabetic ulcer, microangiopathy or small vessel disease, hypothyroidism, thrombotic thrombocytopenic purpura, ischemia-reperfusion injury and haemolytic uraemic syndrome. In one embodiment, the patient suffers from a dementia that is not Alzheimer's Disease. In another embodiment, the patient suffers from microangiopathy or small vessel disease that is not related to diabetes.

In further embodiments, the patient suffers from a disease selected from the group consisting of Pneumotosis intestinalis, Susac's syndrome, microvascular impairment during chronic catheterization, Hamartomatous disease, Blood spinal cord barrier dysfunction following spinal cord injury, corneal perforation, paraneoplastic disease, rhabdomyolysis, pulmonary capillaritis, chronic hyperhomocysteinemia, frontal-subcortical syndrome, Wegener's granulomatosis and acute intestinal microvascular dysfunction.

In some embodiments, the atherosclerotic disease is selected from the group consisting of atherosclerosis of the renal vasculature, cardiac vasculature, brain vasculature and peripheral vasculature.

In some aspects, the patient suffers from a fibrotic condition. In one embodiment, idiopathic pulmonary fibrosis (IPF). Prior patent applications relating to the use of pirfenidone in IPF patients include WO-2007/064738, WO-2007/038315, WO-2008/077068, WO-2010/054294, PCT/US2010/058936, and PCT/US2010/058943, each of which is incorporated by reference herein in its entirety.

As used herein, "concomitant use" is understood to be interchangeable with concurrent administration or co-administration. Thus, the terms are understood to encompass administration simultaneously, or at different times, and by the same route or by different routes, as long as the two agents are given in a manner that allows both agents to be affecting the body at the same time. For example, concomitant use can refer to a medication concomitantly administered, whether prescribed by the same or a different practitioner, or for the same or a different indication.

Adjunct/Combination Therapy

The disclosure contemplates that one or more additional agents are co-administered with pirfenidone or pirfenidone analog therapy. The additional therapeutic, for example, may an immunosuppressive agent, an antioxidant or antioxidant gene regulator, and an anti-inflammatory agent.

The term "immunosuppressive agent" as used herein for adjunct therapy refers to substances that act to suppress or mask the immune system of the mammal being treated herein. This would include substances that suppress cytokine production, downregulate or suppress self-antigen expression, or mask the MHC antigens. In various embodiments, the immunosuppressive agent is selected from the group consisting of a steroid, cyclosporine, cyclosporine analogs, cyclophosphamide methylprednisone, prednisone, azathioprine, tacrolimus (FK-506), 15-deoxyspergualin, rapamycin, mycophenolic acid and sirolimus.

Further examples of immunosuppressive agents contemplated by the disclosure include without limitation 2-amino-6-aryl-5-substituted pyrimidines (see U.S. Pat. No. 4,665,077, the disclosure of which is incorporated herein by reference); nonsteroidal antiinflammatory drugs (NSAIDs); azathioprine; cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; methotrexate (oral or subcutaneous); hydroxycloroquine; sulfasalazine; leflunomide; cytokine or cytokine receptor antagonists including anti-interferon-γ, -β, or -α antibodies, anti-tumor necrosis factor-α antibodies (infliximab or adalimumab), anti-TNF-α immunoahesin (etanercept), anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); and T cell receptor antibodies (EP 340,109) such as T10B9.

In further embodiments, pirfenidone or pirfenidone analog is co-administered with an antioxidant and/or antioxidant gene regulator. The antioxidant and/or antioxidant gene regulator is selected from the group consisting of vitamin C, vitamin E, beta-carotene, new Ets-related factor-2 (NERF-2), N-acetyl cysteine (NAC), bardoxolone, lutein, zinc, selenium and copper.

In still further embodiments, pirfenidone or pirfenidone analog is co-administered with an anti-inflammatory agent. The anti-inflammatory agent is selected from the group consisting of azithromycin, a nonsteroidal anti-inflammatory drug (NSAID) a steroidal anti-inflammatory drug (SAID), a tumor necrosis factor (TNF) inhibitor, and an anti-inflammatory cytokine. In some embodiments, the non steroidal anti-inflammatory carboxylic acid (NSAID) is selected from the group consisting of the propionic acids, the acetic acids, the fenamic acids and the biphenyl carboxylic acids. In various embodiments, the NSAID is selected from an aryl propionic acid, ibuprofen, indoprofen ketoprofen, naproxen, benoxaprogen, flurbiprofen, fenoprofen, fenbufen, pirprogen, carprofen, oxaprozin, pranoprofen, miroprofen, tioxaprofen, suprofen, alminoprofen, tiaprofen, fluprofen, bucloxic acid, sulindac, tolmetin, zomepirac, diclofenac, fenclofenac, alclofenac, ibufenac, isoxepac, furofenac, tiopinac, zidometacin, acematacin, fentiazac, clidanac, oxpinac, fenflozic acid, mefanamic acid, meclofenamic acid, flufenamic acid, niflumic acid, and tolfenamic acid.

Anti-inflammatory agents include, but are not limited to, cytokines, corticosteroids, e.g., lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or higher potency corticosteroids such as clobetasol propionate, betamethasone benzoate, betamethasone diproprionate, diflorasone diacetate, fluocinonide, mometasone furoate, triamcinolone acetonide, and mixtures thereof.

In some embodiments, the anti-inflammatory cytokine is selected from the group consisting of IL-10 and IL-11.

Other examples of anti-inflammatory agents include agents that inhibit tumor necrosis factor (TNF) activity, such as adalimumab (HUMIRA®), infliximab (REMICADE®), certolizumab (CIMZIA®), golimumab (SIMPONI®), and etanercept (ENBREL®).

In some aspects, the pirfenidone or pirfenidone analog is co-administered with a therapeutically effective amount of a hypoxia inducible factor-prolyl hydroxylase inhibitor (HIF-PHI).

In any aspect or embodiment of the disclosure, the additional therapeutic agent is selected from the group comprising one or more of steroids (including but not limited to prednisolone), cytotoxic agents (including but not limited to azathioprine and cyclophosphamide), bardoxolone, LPA antagonists, for example LPA1 (including but not limited to AM152); Torisel (temsirolimus); PI3K inhibitors (including but not limited to GSK2126458); pentraxin (including but not limited to Pentraxin-2 (PTX-2 or PRM-151)); MEK inhibitors (including but not limited to ARRY-162 and ARRY-300); p38 inhibitors; PAI-1 inhibitors (including but not limited to Tiplaxtinin); agents that reduce the activity of transforming growth factor-beta (TGF-β) (including but not limited to pan TGF-β neutralizing antibodies, such as GC-1008 (Genzyme/MedImmune); anti-TGF-β2 mAbs, such as lerdelimumab (CAT-152; Trabio, Cambridge Antibody); anti-TGF-β1 antibodies, such as metelimumab (CAT-192, Cambridge Antibody); small molecule TGF-βR1 inhibitors, such as LY-2157299 (Eli Lilly); ACU-HTR-028 (Opko Health)) including antibodies that target one or more TGF-β isoforms, inhibitors of TGF-β receptor kinases TGFBR1 (ALK5) and TGFBR2, and modulators of post-receptor signaling pathways; modulators of chemokine receptor signaling; endothelin receptor antagonists including inhibitors that target both endothelin receptor A and B and those that selectively target endothelin receptor A (including but not limited to ambrisentan; avosentan; bosentan; clazosentan; darusentan; BQ-153; FR-139317, L-744453; macitentan; PD-145065; PD-156252; PD163610; PS-433540; S-0139; sitaxentan sodium; TBC-3711; zibotentan); agents that reduce the activity of connective tissue growth factor (CTGF) (including but not limited to FG-3019, FibroGen), and also including other CTGF-neutralizing antibodies, such as FG-3019; matrix metalloproteinase (MMP) inhibitors (including but not limited to MMPI-12, PUP-1 and tigapotide triflutate, and doxycycline, marimastat, and cipemastat); agents that reduce the activity of epidermal growth factor receptor (EGFR) including but not limed to erlotinib, gefitinib, BMS-690514, cetuximab, antibodies targeting EGF receptor, inhibitors of EGF receptor kinase, and modulators of post-receptor signaling pathways; agents that reduce the activity of platelet derived growth factor (PDGF) (including but not limited to Imatinib mesylate (Novartis)) and also including PDGF neutralizing antibodies, antibodies targeting PDGF receptor (PDGFR), inhibitors of PDGFR kinase activity, and post-receptor signaling pathways; inhibitors of multiple receptor kinases such as BIBF-1120 which inhibits receptor kinases for vascular endothelial growth factor, fibroblast growth factor, and platelet derived growth factor; agents that interfere with integrin function (including but not limited to STX-100 and IMGN-388) and also including integrin targeted antibodies; agents that interfere with the pro-fibrotic activities of IL-4 (including but not limited to AER-001, AMG-317, APG-201, and sIL-4Rα) and IL-13 (including but not limited to AER-001, AMG-317, anrukinzumab, CAT-354, cintredekin besudotox, MK-6105, QAX-576, SB-313, SL-102, and TNX-650) and also including neutralizing antibodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly pseudomonas endotoxin, signaling though the JAK-STAT kinase pathway; agents that interfere with epithelial mesenchymal transition including inhibitors of mTor (including but not limited to AP-23573 or rapamycin); agents that reduce oxidative stress including N-acetyl cysteine and tetrathiomolybdate; and interferon gamma. Also contemplated are agents that are inhibitors of phosphodiesterase 4 (PDE4) (including but not limited to Roflumilast); inhibitors of phosphodiesterase 5 (PDE5) (including but not limited to mirodenafil, PF-4480682, sildenafil citrate, SLx-2101, tadalafil, udenafil, UK-369003, vardenafil, and zaprinast); or modifiers of the arachidonic acid pathway including cyclooxygenase and 5-lipoxegenase inhibitors (including but not limited to Zileuton). Further contemplated are compounds that reduce tissue remodeling or fibrosis including prolyl hydrolase inhibitors (including but not limited to 1016548, CG-0089, FG-2216, FG-4497, FG-5615, FG-6513, fibrostatin A (Takeda), lufironil, P-1894B, and safironil) and peroxisome proliferator-activated receptor (PPAR)-gamma agonists (including but not limited to pioglitazone and rosiglitazone). Agents also include an agent selected from BG-12, chemokine activity modulators (including but not limited to CNTO 888, an antibody targeting CCL2), Lysl oxidase inhibitors (including but not limited to AB0024/GS-6624, an antibody targeting human lysyl oxidase-like 2), NOX4 inhibitors (including but not limited to GKT137831, a selective NOX ¼ inhibitor), angiotensin II receptor antagonists (including but not limited to lorsartan), and an LPA1/LPA3 antagonist (including but not limited to SAR-100842).

In any aspect disclosed herein, the methods or uses further comprise administering to the patient a therapeutically effective amount of a complement inhibitor. In some embodiments, the complement inhibitor is selected from the group consisting of Eculizumab/Soliris (Alexion), Pexelizumab (Alexion), Mubodina (Adienne), Ergidina (Adienne), ARC1905 (Archemix/Ophthotech), C5aIP/Pep-A (Tohoku University), TNX-558 (Tanox/Genentech), MBP-C5a (Resistentia/Karolinska Institute), C089 (Merck), 3D53/PMX53 (Promics/Cephalon), PMX205 (Promics/Cephalon), JPE-1375 (Jerini), JSM-7717 (Jerini), CGS 27913 (Novartis), CGS 32359 (Novartis), $A8^{A71-73}$ (Medical School Hannover), W-54011 (Mitsubishi Pharma), NDT 9520492 (Neurogen), NGD-2000-1 (Neurogen), NDT 9513727 (Neurogen), a non-peptide CD88 antagonist, CCX168 (ChemoCentryx), NOX-D14 (Noxxon Pharma), Neutrazumab (G2 Therapies/Novo Nodisk), ADC-1004 (Alligator Bioscience), comstatin, a C3, C5 or C5a inhibitor peptide, a C3, C5 or C5a antibody and fragments thereof.

In preferred embodiments, the additional therapeutic agent also preserves or improves microvascular integrity and/or function. A combination of any of the therapeutic agents provided herein is also contemplated.

Dosing and Dose Modifications

In each of the embodiments of the methods described herein, a method of administering pirfenidone is provided to a patient in need thereof. In some embodiments, pirfenidone is administered three times per day with food. In further embodiments, pirfenidone is administered twice a day or once a day, each with food. For example, pirfenidone may be administered once a day or twice a day, each with food.

Pirfenidone can be dosed at a total amount of about 50 mg to about 4005 mg, or about 1000 to about 4000 mg pirfenidone, or about 1800 mg to about 3600 mg pirfenidone, or about 1800 to about 2500 mg pirfenidone, or about 2200 to about 2600 mg pirfenidone. The dosage can be divided into two or three doses over the day or given in a single daily dose. In some embodiments, three capsules of pirfenidone, each capsule comprising about 267-mg of pirfenidone, are administered three times per day. Specific amounts of the total daily amount of the therapeutic contemplated for the disclosed methods include about 50 mg, about 100 mg, about 150 mg, about 200 mg, about 250 mg, about 267 mg, about 300 mg, about 350 mg, about 400 mg, about 450 mg, about 500 mg, about 534 mg, about 550 mg, about 600 mg, about 650 mg, about 700 mg, about 750 mg, about 800 mg, about 801 mg, about 850 mg, about 900 mg, about 950 mg, about 1000 mg, about 1050 mg, about 1068 mg, about 1100 mg, about 1150 mg, about 1200 mg, about 1250 mg, about 1300 mg, about 1335 mg, about 1350 mg, about 1400 mg, about 1450 mg, about 1500 mg, about 1550 mg, about 1600 mg, about 1602 mg, about 1650 mg, about 1700 mg, about 1750 mg, about 1800 mg, about 1850 mg, about 1869 mg, about 1900 mg, about 1950 mg, about 2000 mg, about 2050 mg, about 2100 mg, about 2136 mg, about 2150 mg, about 2200 mg, about 2250 mg, about 2300 mg, about 2350 mg, about 2400 mg and about 2403 mg, or any range of doses between any of these endpoints.

Dosages of pirfenidone can alternately be administered as a dose measured in mg/kg. Contemplated mg/kg doses of the disclosed therapeutics include about 1 mg/kg to about 40 mg/kg. Specific ranges of doses in mg/kg include about 1 mg/kg to about 30 mg/kg, about 5 mg/kg to about 30 mg/kg, about 10 mg/kg to about 40 mg/kg, about 10 mg/kg to about 30 mg/kg, and about 15 mg/kg to about 35 mg/kg.

In one embodiment, a dosage amount of pirfenidone is taken with food. In another embodiment, the patient is instructed to administer the dosage of pirfenidone with food.

Packages, Kits, Methods of Packaging, and Methods of Delivering

In another aspect, a package or kit is provided comprising pirfenidone or pirfenidone analog, optionally in a container, and a package insert, package label, instructions or other labeling including instructions or directions for any of the methods disclosed herein.

The package insert, package label, instructions or other labeling may further comprise directions for treating a patient in need of pirfenidone or pirfenidone analog, e.g. with a microvascular disorder or any other disorder or disease disclosed herein by administering pirfenidone or pirfenidone analog, e.g., at a dosage of 2400 mg or 2403 mg per day.

In a related aspect, the disclosure provides a method of preparing or packaging a pirfenidone or pirfenidone analog medicament comprising packaging pirfenidone or pirfenidone analog, optionally in a container, together with a package insert or package label or instructions for any of the methods disclosed herein.

In some embodiments, a method of treating a patient in need of pirfenidone or pirfenidone analog is disclosed comprising providing, selling or delivering any of the kits of disclosed herein to a hospital, physician or patient.

The disclosure will be more fully understood by reference to the following examples which detail exemplary embodiments of the disclosure. They should not, however, be construed as limiting the scope of the disclosure. All citations throughout the disclosure are hereby expressly incorporated by reference.

EXAMPLES

Example 1

The results below indicate that pirfenidone preserves a healthy microvasculature. Pirfenidone was shown to limit ischemia resulting from allograft rejection and to preserve vascular perfusion and tissue oxygenation.

Figure 1B:
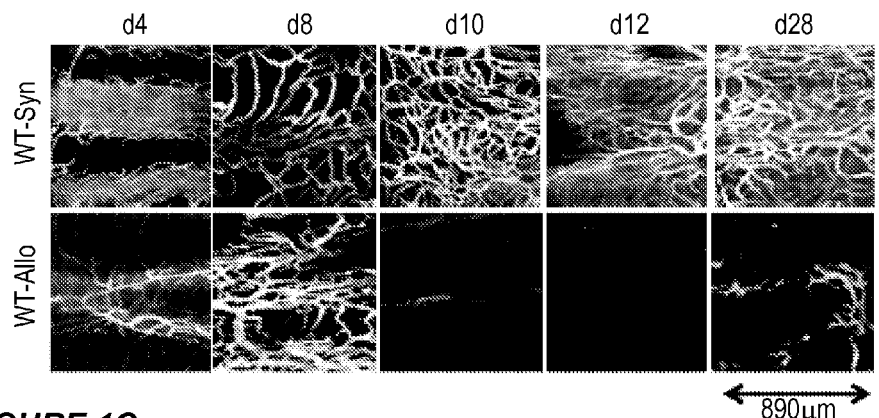
FIG. 1B depicts representative magnified images of blood vessels in the syngeneic (WT-Syn) and allogeneic (WT-Allo) grafts after i.v. injection of FITC-conjugated (green) tomato lectin to bind and identify perfused vasculature, carried out at day 4, day 8, day 10, day 12 and day 28. Allografts consistently lose perfusion by day 10.
Figure 1C:
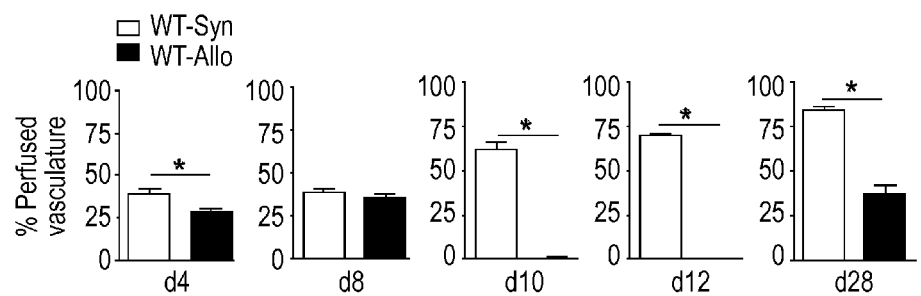
FIG. 1C shows the percentage area of perfused vessels, using a mask based on FITC threshold to mark blood vessels.

Pirfenidone was tested in a murine orthotopic tracheal transplant model, as generally described in Babu et al., *J Clin Invest.* 2007; 117(12):3774-3785. In this model in which allograft rejection occurs, typically perfusion ceases after a fixed period of time which is highly reliable (10 days). FIG. 1A shows that tissue oxygenation for allografted mice dramatically decreases during a time period that begins after day 6 post-transplantation. Perfusion is later restored on rejecting allografts as recipient-derived vessels neovascularize the transplant on d28. In contrast, mice receiving syngeneic (identical) grafts maintain tissue oxygenation at approximately the same levels throughout. Magnified images of the microvasculature, obtained after i.v. injection of FITC-conjugated (green) tomato lectin to bind and identify perfused vasculature, are shown in FIG. 1B. Notably, perfusion is completely lost at day 10. FIG. 1C depicts the percent area of perfused blood vessels, using a mask based on FITC threshold to mark blood vessels, and also shows that the mice receiving allograft experience a loss of perfusion starting at day 10.

Figure 2:
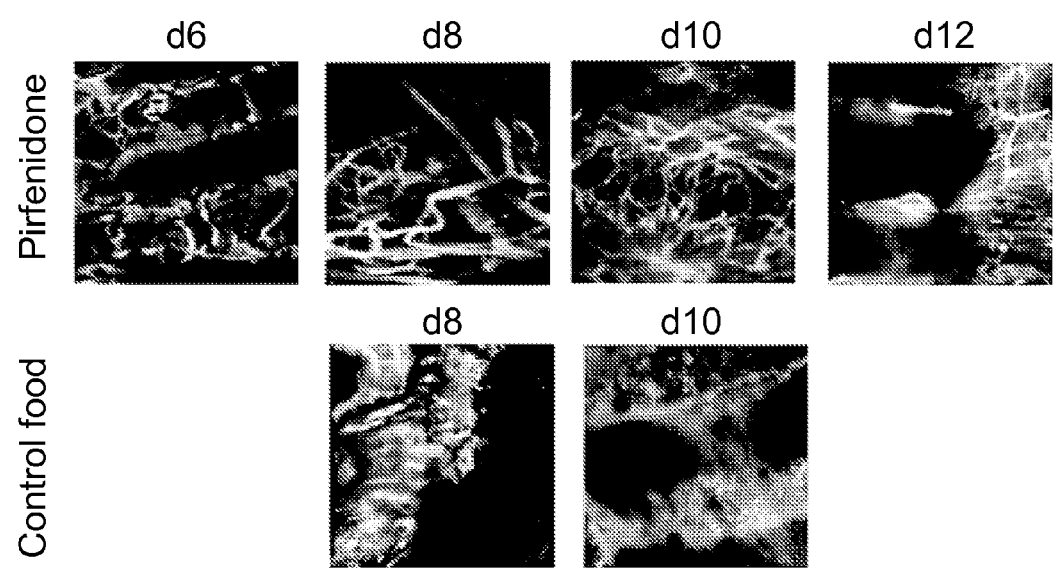
FIG. 2 depicts representative magnified images of blood vessels in a pirfenidone-treated allografted mouse (day 6, 8, 10 and 12 post-transplantation) and a control allografted mouse receiving no treatment (day 8 and 10 post-transplantation). Mice were injected i.v. with FITC-conjugated (green) tomato lectin to bind and identify perfused vasculature.
Figure 3:
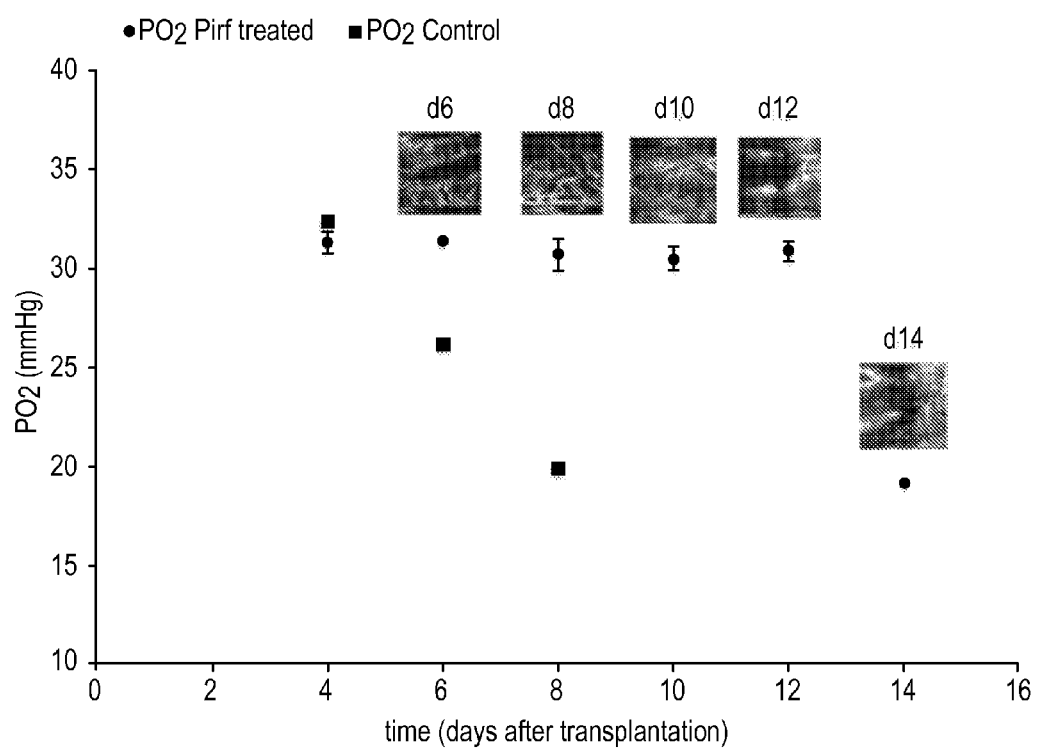
FIG. 3 shows oxygenation levels ($pO_2$ in mmHg) in pirfenidone-treated allografted mice (diamonds) and in control allografted mice receiving no treatment (squares), plotted over time (days post transplantation). Corresponding images of perfused vasculature are also shown next to the data points. Pirfenidone treatment was able to preserve vasculature until at least 12 days post-transplantation.

When allograft recipients are fed pirfenidone ("Pirfenidone" in FIG. 2 in their chow, the vasculature is protected and fibrosis appears to be significantly attenuated. Magnified images of microvasculature of pirfenidone-treated and control mice, obtained after i.v. injection of FITC-conjugated (green) tomato lectin to bind and identify perfused vasculature, are shown in FIG. 2. The vasculature appears robust at both days 10 and 12. FIG. 3 shows tissue oxygenation ($pO_2$ in mm Hg) of the pirfenidone-treated mice receiving allografts, and control mice receiving allografts. FIG. 3 also displays the corresponding images of perfused vasculature next to the data points. FIG. 3 shows that transplant oxygenation correlates with vasculature perfusion. FIG. 3 demonstrates that pirfenidone confers significant protection on the microvasculature and on tissue oxygenation. Pirfenidone treatment was able to preserve vasculature until at least 12 days post-transplantation, and maintained tissue oxygenation at approximately the same levels throughout the time period shown.

What is claimed is:

1. A method for preserving or improving microvascular integrity or treating a microvascular disorder in a patient suffering from bronchiolitis obliterans, comprising administering pirfenidone to the patient, wherein the pirfenidone is administered to the patient prior to diagnosis/onset/showing signs or symptoms of fibrosis.

2. A method for preserving or improving microvascular integrity or treating a microvascular disorder in a patient suffering from bronchiolitis obliterans, comprising administering pirfenidone to the patient, wherein the pirfenidone is administered three times per day, with food.

3. A method for preserving or improving microvascular integrity or treating a microvascular disorder in a patient suffering from bronchiolitis obliterans, comprising administering pirfenidone to the patient, wherein the amount effective to preserve or improve microvascular integrity or treat the microvascular disorder is about 2400 or 2403 mg/day and wherein the pirfenidone is administered three times per day, with food.

* * * * *

UNITED STATES PATENT AND TRADEMARK OFFICE
CERTIFICATE OF CORRECTION

PATENT NO. : 9,682,071 B2  
APPLICATION NO. : 14/772241  
DATED : June 20, 2017  
INVENTOR(S) : Nicolls et al.

Page 1 of 1

It is certified that error appears in the above-identified patent and that said Letters Patent is hereby corrected as shown below:

On the Title Page

At Column 1, item (73), the Assignee should be:
--INTERMUNE, INC., Brisbane, CA (US); THE BOARD OF TRUSTEES OF THE LELAND STANFORD JUNIOR UNIVERSITY, Palo Alto, CA (US); DEPARTMENT OF VETERANS AFFAIRS, Washington, D.C. (US)--

Signed and Sealed this
Twenty-first Day of August, 2018

Andrei Iancu
*Director of the United States Patent and Trademark Office*